(12) United States Patent
Engelmayr, Jr. et al.

(10) Patent No.: US 10,363,124 B2
(45) Date of Patent: Jul. 30, 2019

(54) METHODS AND APPARATUSES FOR FORMING FIBROUS TUBES

(71) Applicant: HUMACYTE, INC., Morrisville, NC (US)

(72) Inventors: George C. Engelmayr, Jr., Raleigh, NC (US); Laura E. Niklason, Greenwich, CT (US); Shannon L. Dahl, Palo Alto, CA (US); Justin T. Strader, Durham, NC (US); Jinlin Zhang, Raleigh, NC (US); Stuart Irwin, Denver, CO (US)

(73) Assignee: HUMACYTE, INC., Durham, NC (US)

( * ) Notice: Subject to any disclaimer, the term of this patent is extended or adjusted under 35 U.S.C. 154(b) by 0 days.

(21) Appl. No.: 15/512,532

(22) PCT Filed: Sep. 18, 2015

(86) PCT No.: PCT/US2015/051015
§ 371 (c)(1),
(2) Date: Mar. 17, 2017

(87) PCT Pub. No.: WO2016/044762
PCT Pub. Date: Mar. 24, 2016

(65) Prior Publication Data
US 2017/0296323 A1    Oct. 19, 2017

Related U.S. Application Data

(60) Provisional application No. 62/052,236, filed on Sep. 18, 2014.

(51) Int. Cl.
*A61F 2/06* (2013.01)
*A61L 27/56* (2006.01)
(Continued)

(52) U.S. Cl.
CPC .............. *A61F 2/062* (2013.01); *A61L 27/18* (2013.01); *A61L 27/56* (2013.01); *A61L 27/58* (2013.01);
(Continued)

(58) Field of Classification Search
CPC . B29C 67/0022; B29C 67/0018; B29C 69/02; B29C 33/0033; B29C 2793/0045;
(Continued)

(56) References Cited

U.S. PATENT DOCUMENTS 1,988,640 A * 1/1935 Welsford ........... B29D 99/0035
                                                    156/187
3,372,447 A * 3/1968 Williams ............... D04H 18/02
                                                    28/113
(Continued)

FOREIGN PATENT DOCUMENTS

DE          234043 A1      3/1986
JP    H 10-325072 A       12/1998
(Continued)

OTHER PUBLICATIONS

International Search Report and Written Opinion, dated Jan. 28, 2016, for International Application No. PCT/US2015/051015, filed Sep. 18, 2015.
(Continued)

*Primary Examiner* — Joseph S Del Sole
*Assistant Examiner* — Emmanuel S Luk
(74) *Attorney, Agent, or Firm* — Cooley LLP (57) ABSTRACT

Embodiments of the present disclosure are directed to apparatuses and methods for fabricating tubular structures from a combination of fibrous materials for use in, for example, tissue engineering scaffold applications. These materials may also be useful in other biological or non-biological applications in which such tubular fibrous structures may be
(Continued)

applicable, examples including conventional medical devices, filters, fiber optics, cable wraps, geotextiles, batteries, fuel cells, armor, and other diverse applications.

9 Claims, 3 Drawing Sheets

(51) Int. Cl.
| | | |
|---|---|---|
| *A61L 27/58* | (2006.01) | |
| *B29C 67/00* | (2017.01) | |
| *D04H 5/02* | (2012.01) | |
| *A61L 27/18* | (2006.01) | |
| *D04H 18/02* | (2012.01) | |
| *B29C 53/40* | (2006.01) | |
| *B29K 67/00* | (2006.01) | |
| *B29K 105/00* | (2006.01) | |
| *B29L 23/00* | (2006.01) | |
| *B29L 31/00* | (2006.01) | |
| *B29C 53/42* | (2006.01) | |
| *B29C 53/46* | (2006.01) | |

(52) U.S. Cl.
CPC .......... *B29C 53/40* (2013.01); *B29C 67/0022* (2013.01); *D04H 5/02* (2013.01); *D04H 18/02* (2013.01); *A61F 2220/0075* (2013.01); *A61F 2240/001* (2013.01); *B29C 53/42* (2013.01); *B29C 53/46* (2013.01); *B29K 2067/003* (2013.01); *B29K 2067/043* (2013.01); *B29K 2105/256* (2013.01); *B29L 2023/22* (2013.01); *B29L 2031/7532* (2013.01)

(58) Field of Classification Search
CPC ... B29C 53/42; B29C 53/82; B29C 2043/425; D04H 18/02; D04H 5/02; A61L 27/18; A61L 27/56; A61L 27/58
See application file for complete search history.

(56) References Cited

U.S. PATENT DOCUMENTS

| | | | | |
|---|---|---|---|---|
| 3,988,191 | A * | 10/1976 | Matsui | B29C 53/42 156/214 |
| 4,132,519 | A * | 1/1979 | Reed | B26D 7/086 264/156 |
| 4,743,495 | A | 5/1988 | Lilani et al. | |
| 5,074,352 | A * | 12/1991 | Suzuki | B22D 19/0027 164/120 |
| 5,167,898 | A * | 12/1992 | Luther | B29C 33/0033 249/145 |
| 5,504,979 | A | 4/1996 | Sheehan et al. | |
| 5,755,791 | A | 5/1998 | Whitson et al. | |
| 5,864,931 | A * | 2/1999 | Best | D21F 7/083 139/383 A |
| 5,893,200 | A * | 4/1999 | Fehrer | D04H 18/02 28/107 |
| 5,894,643 | A * | 4/1999 | Fehrer | D04H 18/02 28/107 |
| 5,896,633 | A * | 4/1999 | Fehrer | D04H 18/02 28/103 |
| 6,065,194 | A | 5/2000 | Dilo | |
| 6,158,097 | A * | 12/2000 | Dilo | D04H 1/46 28/107 |
| 6,358,284 | B1 | 3/2002 | Fearnot et al. | |
| 7,594,809 | B2 * | 9/2009 | Satoh | B22F 3/03 425/193 |
| 2004/0207108 | A1 * | 10/2004 | Pacchiana | B29C 43/006 264/109 |
| 2004/0254640 | A1 | 12/2004 | Sutherland et al. | |
| 2006/0084930 | A1 | 4/2006 | Dhanaraj et al. | |
| 2006/0288549 | A1 * | 12/2006 | Jean | D04H 18/02 28/107 |
| 2007/0036842 | A1 | 2/2007 | Spencer | |
| 2007/0120277 | A1 | 5/2007 | Short | |
| 2007/0269481 | A1 | 11/2007 | Li et al. | |
| 2008/0021554 | A1 | 1/2008 | Stone et al. | |
| 2008/0313873 | A1 * | 12/2008 | Link | D04H 18/02 28/108 |
| 2009/0209982 | A1 | 8/2009 | Hoerstrup et al. | |
| 2011/0282364 | A1 | 11/2011 | Moloye-Olabisi et al. | |
| 2013/0217554 | A1 * | 8/2013 | Hanyu | B65G 39/00 492/33 |
| 2013/0317285 | A1 | 11/2013 | Soletti et al. | |
| 2013/0345824 | A1 | 12/2013 | Dahl et al. | |
| 2014/0141152 | A1 | 5/2014 | Sostek et al. | |
| 2014/0159280 | A1 * | 6/2014 | Martin | B29C 33/0033 264/299 |
| 2018/0021984 | A1 * | 1/2018 | Huang | B29C 33/0033 |

FOREIGN PATENT DOCUMENTS

| | | |
|---|---|---|
| JP | 2002-263390 A | 9/2002 |
| WO | WO 2012/094611 A1 | 7/2012 |

OTHER PUBLICATIONS

Dahl, Shannon, L.M. et al., "Readily Available Tissue-Engineered Vascular Grafts", Science Translational Medicine Feb. 2, 2011, vol. 3, Issue 68, pp. 68ra9 (1-11).

Freed, L.E. et al., "Biodegradable polymer scaffolds for tissue engineering", Bio/Technology (N.Y.), vol. 12, Jul. 1994, pp. 689-693.

Niklason, L.E. et al., "Functional Arteries Grown in Vitro", Science Apr. 16, 1999, vol. 284, Issue 5413, pp. 489-493.

Dahl, Shannon L.M. et al., "Decellularized Native and Engineered Arterial Scaffolds for Transplantation." Cell Transplantation, vol. 12, No. 6, 2002, pp. 659-66(8).

Examination Report, dated Sep. 19, 2017, for Australian Application No. 2015317387.

* cited by examiner

3-D Projections of parts in FIG. 2A

FIG. 3

METHODS AND APPARATUSES FOR FORMING FIBROUS TUBES

CROSS-REFERENCES TO RELATED APPLICATIONS

This application is a National Phase of PCT Patent Application No. PCT/US2015/051015 having International filing date of Sep. 18, 2015, which claims benefit of and priority to U.S. Provisional Patent Application No. 62/052,236, entitled, "Methods and Apparatuses for Forming Fibrous Tubes," filed Sep. 18, 2014, the disclosures of which are herein incorporated by reference in their entireties.

BACKGROUND

Fibrous Scaffolds, and in particular, those used for tissue engineering applications, can be derived from natural and biological materials or they can be fabricated from synthetic polymers. Scaffolds may also contain metallic and/or mineral components, especially for applications involving hard tissues such as bones. Scaffolds provide a support structure amenable to cellular attachment, proliferation, and extracellular matrix synthesis and deposition.

SUMMARY OF SOME OF THE EMBODIMENTS

Exemplary embodiments of the present disclosure are directed to methods and systems for forming tubular scaffolds for tissue engineering. Methods and apparatuses disclosed herein may also be applicable to fibrous tubular structures for other applications, including, but not limited to, conventional medical devices, filters, fiber optics, cable wraps, geotextiles, batteries, fuel cells, armor, and other diverse applications. In some embodiments, a method is provided which comprises providing a strip of scaffolding material (e.g., fibrous material), with the strip including a length, width, and thickness, and corresponding edges thereto. Examples of scaffolding materials include fibrous materials, such as, but not limited to, non-woven felts, wovens, knits, electrospuns, and other fibrous or fiber-like materials made from synthetic or naturally-derived, thermoplastic, thermoset, or ionomer (e.g., Nafion), degradable and substantially non-degradable polymers, metals (e.g., Nitinol) and glasses (e.g., silica-based glass and other optical fibers), including, but not limited to, polyesters such as polyglycolic acid, poly-L-lactic acid, polylactic-co-glycolic acid, polyglycerol sebacate, polycaprolactone, polyhydroxybutyrate, and polyethylene terephthalate, polyamides, polyurethanes, polyanhydrides, and naturally-derived polymers, such as silks, collagens, elastins, chitosans, fibrins, and other naturally-derived polymers.

In some embodiments, the method includes aligning a first lengthwise edge of the strip immediately adjacent to a second lengthwise edge of the strip to form a tubular structure, where the two adjacently positioned lengthwise edges form a lengthwise boundary. In some implementations, the method also includes tangentially puncturing the tubular structure proximate to and along the boundary from at least one side of the boundary with at least one needle such that a portion of one or more fibers from the strip near at least one of the lengthwise edges traverses the boundary and intertwines with one or more fibers from the strip near the other lengthwise edge, thereby forming a seam. In some embodiments, the tangential puncturing may be performed from both sides of the boundary.

In some embodiments, the scaffolding material comprises a range of sizes, shapes and densities. For example, a strip of the scaffolding material used for scaffolding applications may range in width from about 0.5 cm to about 15 cms, in length from about 1 cm to about 100 cms, in thickness from about 0.25 mm to about 2 mm, and in density from about 10 mg/cc to about 100 mg/cc. In some embodiments, the needles used in attaching the scaffolding material strips may range in gauge from about 32 (i.e., about 0.65 mm) to about 43 (i.e., about 0.38 mm), may have different numbers of barbs per needle (e.g., 1 to 20), may have different spacing between the barbs of each needle (e.g., 2 mm to 20 mm), may have different size barbs, and may have different blade shapes (e.g., triangular, crown, spiral, conical, etc.). In some embodiments, the needles may have either forward or reverse barbs, or combinations of forward and reverse barbs on the same needle. For example, in an exemplary embodiment, a 42 gauge (i.e., about 0.4 mm) chrome-plated triangular blade felting needle may be used to attach a biodegradable material to a non-biodegradable material, or different sections of a biodegradable material to each other.

In some embodiments, in tangentially puncturing the tubular structure, a plurality of needles may be used for puncturing. In some embodiments, tangential puncturing of the tubular structure may be effected without the use of needles, for example, through a single or plurality of high pressure gas or fluid jets (i.e., hydro-entangled); in other embodiments, tangential bonding of the fibrous tubular structure may be effected through a single or plurality of lasers (e.g., $CO_2$ lasers or other lasers capable of melt-fusing fibers with or without additional binders). In an exemplary embodiment, for example, these needles may comprise needles with barbed triangular blades arranged in a linear array; and the faces of the barbed triangular blades of the plurality of needles may be oriented substantially identically. In some embodiments, the plurality of needles includes forward felting needles and reverse felting needles. In some embodiments, the plurality of needles may be oriented at an angle from about 0 degrees to about 90 degrees relative to the long axis of the tubular structure. In the linear array, in some embodiments, the needles may be arranged so that the tip-to-tip distance between the needles ranges from about 1 mm to about 10 mm. In some implementations, the puncturing may be done electromechanically and/or manually, and an exemplary embodiment comprises advancing and retracting the needles so as to eventually penetrate each lengthwise edge of the strip of the scaffolding material substantially perpendicularly. In some embodiments, in between instances of puncturing the tubular structure by, for example, advancing and retracting the at least one needle, the at least one needle may be moved longitudinally along the lengthwise boundary.

In some embodiments of the present disclosure, an exemplary system for forming tubular scaffolds for tissue engineering is disclosed. Such an exemplary system may comprise a mandrel with an outer circumference configured to receive a strip of scaffolding material wound there around. In some embodiments, the system may include at least one first structure configured with at least one first recess that is configured to receive at least a first portion of the circumference of the mandrel with the wound scaffolding material. In some embodiments, there may be at least one channel provided along a length of the first structure. The system may also include at least one second structure configured with at least one second recess that is configured to receive at least a second portion of the circumference of the mandrel with the wound scaffolding material. In some embodiments, there may be at least one channel provided along a length of the second structure and arranged between the internal surface of the second recess and an external surface of the second structure, where the at least one first structure and the at least one second structure are configured for mated arrangement such that upon mating the circumference of the mandrel having the strip of scaffolding material wound there around is substantially encompassed by the first and second recesses. Further, the strip of scaffolding material may be wound around the circumference of the mandrel (or a portion thereof) such that a first lengthwise edge of the strip is aligned immediately adjacent to a second lengthwise edge of the strip to form a tubular structure. In some embodiments, the two adjacently positioned lengthwise edges form a lengthwise boundary, where the lengthwise boundary may be arranged adjacent the channel.

In some embodiments, the at least one needle may be arranged adjacent the channel and may be configured for insertion through the channel to tangentially puncture the tubular structure proximate to and along the boundary from at least one side of the boundary such that a portion of one or more fibers from the strip near at least one of the lengthwise edges traverses the boundary and intertwines with one or more fibers from the strip near the other lengthwise edge thereby forming a seam. In some implementations, there may be a plurality of needles puncturing the tubular structure. These needles, comprising barbed triangular blades, may be arranged in a linear array. In some embodiments, the faces of the barbed triangular blades of the plurality of needles may be oriented substantially identically.

In some implementations, the system may further comprise an electromechanical, pneumatic, or otherwise mechanized actuator or motor configured to insert and retract the at least one needle through the channel repeatedly (which may also be referred to, in some embodiments, "needle movement means"). In some embodiments, such needle movement means may also be configured to move the at least one needle longitudinally along the channel. In some embodiments, prior to the tangential puncturing of the tubular structure, the means may position the at least one needle at a determined distance from the tubular structure of about 0.1 cm to about 5 cm (for example).

In some embodiments, the system further comprises a partial-cylindrical third structure with a diameter substantially equal to an outer diameter of the mandrel with the strip of scaffolding material wound there around. In some embodiments, the third structure may be shaped differently than a circular cylinder, having, for example, a cross-section of a partial square, partial hexagon, or other open or closed shape (e.g., geometric shape). The third structure may be configured to comb over one of the first lengthwise edge of the strip and the second lengthwise edge of the strip so as to align the first lengthwise edge of the strip and the second lengthwise edge of the strip immediately adjacent to each other to form the tubular structure.

In some embodiments, a fibrous tube configured for establishing a scaffold for tissue engineering is provided and comprises a strip of scaffolding material. The strip includes a length and a width and corresponding edges thereto. A first lengthwise edge of the strip is aligned immediately adjacent to a second lengthwise edge of the strip to form a tubular structure, the two adjacently positioned lengthwise edges forming a lengthwise boundary. The lengthwise boundary forms a seam having a plurality of punctures among the lengthwise edges, where the punctures are configured with one or more fibers from at least one of the lengthwise edges traversing the boundary and intertwining with one or more fibers from the other lengthwise edge.

Further to such fibrous tube embodiments, such embodiments may further include one and/or another of the following features/structure/functionality:

the scaffolding material comprises a fibrous material;

the scaffolding material is selected from the group consisting of non-woven polyglycolic acid (PGA) felt and nonwoven polyethylene terephthalate (PET) felt;

the width of the strip of the scaffolding material ranges from about 0.5 cm to about 15 cm, the length of the strip of the scaffolding material ranges from about 1 cm to about 100 cm, and thickness of the strip of the scaffolding material ranges from about 0.25 mm to about 2 mm;

the punctures are sized according to the gauge of the felting needles, which range from about 32 gauge (i.e., about 0.65 mm) to about 43 gauge (i.e., about 0.38 mm);

the center-to-center distance of punctures ranges from about 1 mm to about 10 mm; and the length of the punctures from within one edge to the other is about 1 cm.

Other embodiments of the present disclosure are directed to biologically-related and non-biologically related products including, but not limited to, medical devices, filters, fiber optics, cable wraps, geotextiles, batteries, fuel cells, and armor (for example), comprising, fibrous materials constructed according to one and/or another of some of the disclosed embodiments.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION OF SOME OF THE EMBODIMENTS

Tissue engineering scaffolds are generally characterized as three-dimensional, porous, biocompatible and biodegradable materials capable of accommodating the attachment of living biological cells. In general, scaffolds for soft tissue applications can be derived from natural, biological materials (e.g., collagen, fibrin gels, etc.), or they can be fabricated from synthetic polymers (e.g., poly(glycolic acid), poly(glycerol sebacate), etc.); scaffolds for hard tissue applications, such as bone, may also include metallic and/or mineral components. The three-dimensional structure of the scaffold, both at the macroscopic scale of the native tissue gross anatomy, as well as at the microscopic scale of the cells, may be fabricated from the aforementioned naturally-derived or synthetic materials by an ever-growing variety of methods, including traditional textile methods such as weaving or knitting, as well as using more recent technologies, such as 3-D printing.

An exemplary purpose of a scaffold is to provide a temporary support structure amenable to cellular attachment, proliferation, and extracellular matrix synthesis and deposition. Scaffolds may be designed to mimic the shape and size of human and/or animal anatomical structures (e.g., tubes in the case of vascular structures). The surface chemistry and degradation behaviors of the scaffold materials-of-construction may be considered useful in ensuring wettability by aqueous fluid media, protein adsorption, cellular attachment, viability, and phenotype, as well in ensuring stability of structural and mechanical properties of the de novo formed tissue during the time-course of culture, by balancing the rate of extracellular matrix deposition and maturation with the rate of scaffold degradation. Pore size and pore interconnectivity may also be useful in ensuring cellular penetration and attachment throughout the thickness of the scaffold and adequate tissue interconnectivity between distant regions of the scaffold. Further, uniformity of the scaffold structure, when considered at a particular length-scale, may be desirable to ensure uniformity of properties and function of the tissue formed upon it.

An example of a synthetic material applied as a tissue engineering scaffold is needle-punched nonwoven poly(glycolic acid). Nonwoven PGA, also commonly referred to as PGA felt or PGA mesh, was introduced as a tissue engineering scaffold by Freed L E, Vunjak-Novakovic G, Biron R J, Eagles D B, Lesnoy D C, Barlow S K, Langer R. (Biodegradable polymer scaffolds for tissue engineering. *Biotechnology* (N.Y.). 1994 July; 12 (7):689-93). In that study, the nonwoven PGA scaffold was tested in the context of cartilage tissue engineering, demonstrating that chondrocytes could attach to and synthesize extracellular matrix on and within the porous space of these scaffolds.

A study in which a nonwoven PGA scaffold was applied in vascular tissue engineering is that of Niklason L E, Gao J, Abbott W M, Hirschi K K, Houser S, Marini R, Langer R. (Functional arteries grown in vitro. *Science*. 1999 Apr. 16; 284 (5413):489-93). In that study, suspensions of bovine vascular-derived smooth muscle cells were pipetted onto nonwoven PGA scaffolds pre-treated with a solution of sodium hydroxide (to increase hydrophilicity, protein adsorption, and concomitant cell attachment). During a period of 8 weeks culture in a bioreactor, in which pulsatile flow through the lumen imparted cyclic radial strains to the engineered tissue construct, the smooth muscle cells secreted collagens and other extracellular matrix proteins. Subsequently, endothelial cells were seeded into the lumens of the constructs and cultured for an additional three days, after which an essentially confluent endothelium was established, ultimately yielding autologous tissue engineered blood vessels capable of responding to vasoactive molecules in a manner similar to native vessels and capable of being implanted and remaining patent for at least 4 weeks in the right saphenous artery of Yucatan miniature swines.

To address issues associated with autologous cells, Dahl S L, Koh J, Prabhakar V, Niklason L E. (Decellularized native and engineered arterial scaffolds for transplantation. *Cell Transplant*. 2003; 12(6):659-66.) demonstrated that the aforementioned tissue engineered blood vessels based on nonwoven PGA scaffolds and smooth muscle cells could be rendered acellular through a combination of enzymatic and detergent-based treatments.

This fundamentally novel approach introduced by Dahl et al. was further developed by the company Humacyte, culminating in a pre-clinical report by Dahl S L, Kypson A P, Lawson J H, Blum J L, Strader J T, Li Y, Manson R J, Tente W E, DiBernardo L, Hensley M T, Carter R, Williams T P, Prichard H L, Dey M S, Begelman K G, Niklason L E. (Readily available tissue-engineered vascular grafts. *Sci Transl Med*. 2011 Feb. 2; 3 (68):68ra9). In these pre-clinical primate studies, the nonwoven PGA scaffolds were formed from rectangular strips into 6 mm inside diameter cylindrical tubes by a manual entanglement method, in which a single barbed needle was utilized to pull fibers from one side to the opposite side of an interface made between the two edges of a PGA strip wrapped around a mandrel, Dahl et al. WO 2012/094611, "Tissue Engineered Constructs", Filed Jan. 6, 2012.

The aforementioned manual method of forming nonwoven PGA tubes may yield scaffold structures capable of yielding uniform tissue engineered constructs. However there may be challenges related to, for example, the manual nature of the formation of the tubes. For example, formation of uniform seam lines in nonwoven PGA tubes by manual entanglement: (a) may be intrinsically subject to variability in seam line density associated with the individual skill and training of the particular technician (in some embodiments, the density may be within an acceptable density range of 45 to 75 mg/cc), (b) may be time-consuming, for example, requiring up to 1 hour to form a single, about 42 cm long tube, (c) often may generate seam lines that may be difficult to distinguish from the surrounding nonwoven PGA, making it challenging to reliably orient the seam line in a straight line when loading the tube into the bioreactor, and (d) may be intrinsically subject to variability in seam line tensile mechanical properties (e.g., stiffness, strength, strain-to-failure) associated with the individual skill and training of the particular technician. In some embodiments, automated and/or mechanical processes of forming scaffolding tubes (e.g., nonwoven PGA tubes) may be desirable.

Figure 1:
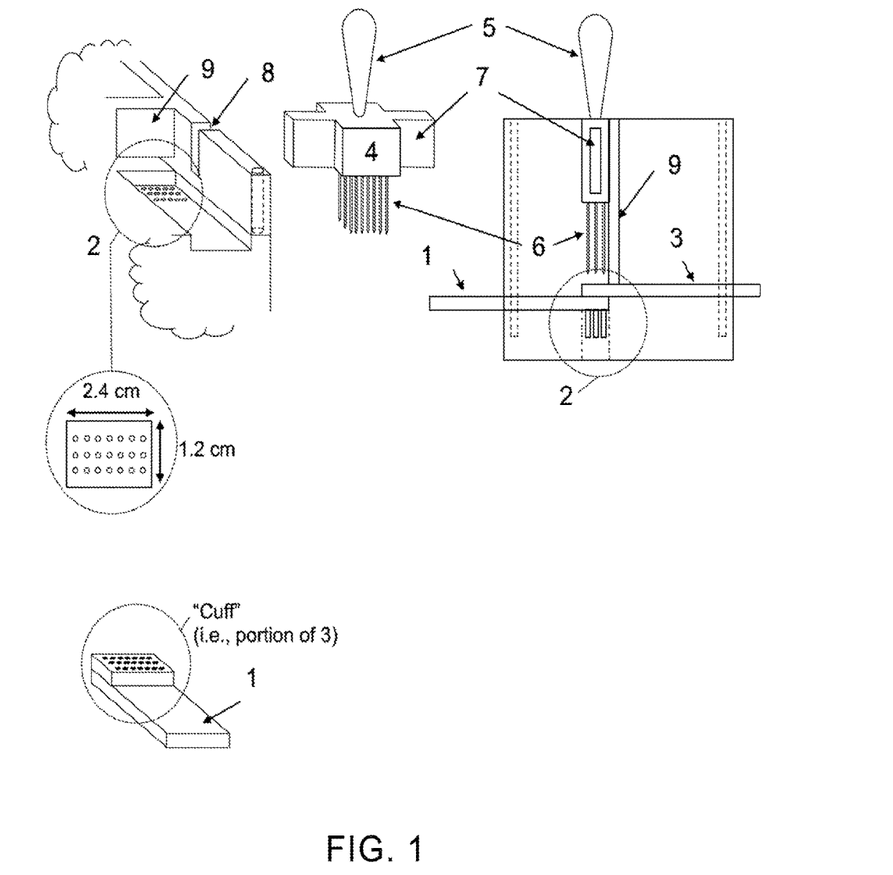
FIG. 1 shows an embodiment of a process to attach fibrous materials together to form a scaffold for tissue engineering purposes.

Referring to FIG. 1, a strip 1 of fibrous scaffold material (an example of which is a degradable nonwoven felt made of poly(glycolic acid) (PGA)) is fed into the lower slot of a "cuff attachment device," such that a portion of the strip's length is positioned over top of a section of the base of the cuff attachment device containing a plurality of holes 2. The strip may have arbitrary dimensions depending on the desired purpose of the to-be-made scaffolding. Exemplary dimensions are width ranging from about 0.5 cm to about 15 cm, length ranging 1 cm to 100 cm, and thickness ranging from about 0.25 mm to about 2 mm thick. For example, a strip for making a tubular scaffold may be 2.4 cm wide, 42 cm long, and 1 mm thick. The portion of the strip's length positioned over the top of a section of the base of the cuff attachment device may be 0.1 cm to 100 cm long; and in some embodiments it may be 1.2 cm. The holes may have any desired shape, size and combinations thereof consistent with the dimensions of the strip. For example, the holes may have circular, square, rectangular, etc., shapes. In some embodiments, the holes may be substantially rectangular, with their long axes perpendicular to the long axes of the fibrous strips. In some embodiments, the holes may have circular shape, and they may be arranged in a regular manner. For example, an arrangement of holes comprises a 3 by 7 array of 21 circular holes, each with diameter 1.5 mm spaced evenly 3 mm apart measured center-to-center in both dimensions.

A second strip 3 of fibrous material (an example of which is a nonwoven felt made of polyethylene terephthalate (PET), to be used as a cuff or extension of the first strip 1) is fed into the upper channel of the cuff attachment device, such that a portion of the strip 3 (0.1 cm to 100 cm; in a preferred embodiment, 1.2 cm) is positioned over top of the portion of the strip 1 situated over top of the section of the cuff attachment device containing the plurality of holes. The second strip may have arbitrary dimensions consistent with the size of the first strip. For example, the second strip may be 0.5 cm to 15 cm wide, 1 cm to 100 cm long, and 0.25 mm to 2 mm thick. For example, to be used as a cuff for the embodiment of the first strip discussed above, the strip may be 2.4 cm wide, 1.2 cm long (e.g., see enlargement 2 in FIG. 1), and 1 mm thick. An exemplary portion of the strip 3 positioned over the top of the portion of the strip situated over top of the section of the cuff attachment device may measure between 0.1 cm to 100 cm, for example, 1.2 cm. It will be appreciated that strip 1 and strip 3 may be switched, that is, strip 1 can be arranged to cover strip 3, or strip 3 may be arranged to cover strip 1 (according to some embodiments).

A movable piece of the cuff attachment device 4, including a knob 5 on top and presenting a plurality of needles 6 (e.g., felting needles) on the bottom, is positioned over top the section of the base of the cuff attachment device. In one embodiment, the movable piece is actuated electromechanically using a motor and lead screw. In some embodiments, the movable piece is actuated manually by way of the hand knob, and it may be configured to move up and down, with sides or projections 7 of the movable piece riding in a vertical slot(s) 8 in the top part of the cuff attachment device that constrain motion of the movable piece to the vertical plane. In another embodiment, the body of the movable piece presenting the felting needles is substantially narrower than the width of the channel and/or substantially shorter than the length of the slot (in some embodiments, substantially less corresponds to less than half the length of the slot), such that the motion is unconstrained in both the vertical, lateral, and/or longitudinal directions, thereby allowing for up and down, side-to-side, and back-and-forth motions, or combinations thereof. In some embodiments, a backstop 9 or other means may be utilized to help align the fibrous materials.

In some embodiments, the movable piece is configured to move at least one of vertically, laterally and longitudinally (and in some embodiments a plurality thereof, and in some embodiments, all). In some embodiments, when the movable piece is pushed down, the plurality of felting needles perforate both layers of fibrous material that may be overlapping. The barbs of the felting needles push and/or pull fibers between the materials 1 and 3, progressively entangling the two materials together as the movable piece is brought back up and down repeatedly a plurality of times, ranging from about 1 to about 20 times. In one embodiment, the felting needles are of a sufficiently large gauge, having a sufficiently high fiber-carrying-capacity (e.g., gauge 32 (i.e., about 0.65 mm) needles), such that only one down and up motion is required to entangle the two materials. In some embodiments, triangular blade, 42 gauge (i.e., about 0.4 mm), chrome-plated felting needles may be utilized, and any number of up and down motions (e.g., anywhere from one to about twenty) may be used to entangle the two materials. In some embodiments, the holes in the base of the cuff attachment device may be rectangular and the movable piece is capable of both up and down and side-to-side motion, the movable piece is pushed down and up and then moved an arbitrary lateral distance (within the constraints of the channel dimensions) before pushing down again, thereby offering the ability to interlace needle penetration sites in the lateral direction.

The top portion of the cuff attachment device may be removed by pulling it up from the alignment pins, allowing the attached materials to be removed from the device. In one embodiment, the attached materials are entangled from only one side. In another embodiment, the 3×7 array of 21 felting needles is comprised of an alternating combination of standard (forward) felting needles that push fiber and retract smoothly, and inverted (reverse) felting needles that insert smoothly and pull fiber, thereby effectively entangling the material from both sides. In some embodiments, the attached materials are removed after being entangled, flipped upside-down, and then entangled from the opposite side (i.e., with the felting needles penetrating from the first strip 1 into the second strip 3). When finished, any excess material (e.g., material beyond the portion entangled together) may be trimmed. In one embodiment, there is no excess material, with the strips being entangled together along their entire length.

Figure 2A:
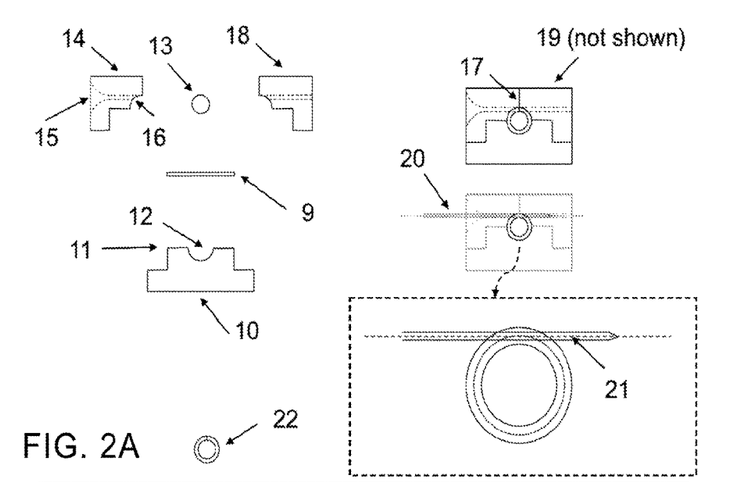
FIG. 2 shows an embodiment of a process to assemble exemplary parts of an apparatus used in forming and shaping tubular structures from scaffolds.
Figure 2B:
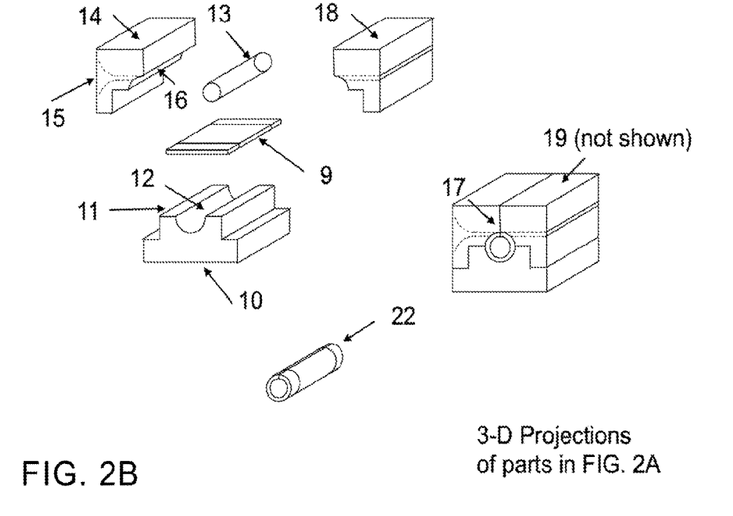

Referring to FIG. 2A and FIG. 2B, the strip 9 (for example, fabricated as described above), comprised of a degradable fibrous material with non-degradable cuff materials attached on both ends, may be positioned on top of a solid support 10 with an upper face 11 whose width is substantially identical to that of the strip (e.g., 2.4 cm wide), whose upper face length is longer than that of the strip (e.g., 50 cm long in the case of a 42 cm long strip), and which includes, centered in the middle of the upper face and running in parallel with the long axis of the support, a hemi-cylindrical groove 12 with a diameter equal to the outside diameter of the tube to be fabricated. In some embodiments, the outside diameter of the tube may have a diameter of 8 mm. The long edges of the strip are aligned in parallel with the long edges of the upper face of the support. One of skill in the art will appreciate that, in some embodiments, the strip of material (e.g., 9 with reference to FIGS. 2A and 2B) may comprise the degradable fibrous material without the non-degradable cuff material.

A mandrel 13 with a diameter less than or equal to the intended inside diameter of the tube to be made (for example, 6 mm diameter and comprising a thin walled silicone tube slide concentrically over top of an inner stainless steel mandrel) is centered over top of the strip and pressed down, bending the strip width-wise around the mandrel as the strip and mandrel are pressed into the hemi-cylindrical groove. The long edges of the strip are now protruding substantially vertically from the hemi-cylindrical groove, from either side of the mandrel.

A holder 14 with a beveled lead-in 15 to a single, substantially rectangular slot 16 running along its length is brought into position from one side of the strip. The holder is pressed laterally against the one of the long edges of the strip, in such a way that when the holder is pressed as far laterally as possible against the solid support, the face of the holder 17 is substantially flush with the long edge of the strip.

A second holder 18, with or without a beveled lead-in to a single, substantially rectangular hole running along its length, is brought into position from the opposite side of the strip. In one embodiment, prior to pressing the second holder as far laterally as possible against the solid support, the long edge of this opposite side of the strip is slightly tucked into the slot 16 of the opposing holder (e.g., using a thin, approximately 1 mm to 2 mm thick metal or plastic piece). In this embodiment, the second long edge is tucked up against the opposing long edge such that the long edges meet at an interface and are substantially non-overlapping. In another embodiment, the second holder 18 is brought into position at an angle such that the second long edge is combed toward the opposing holder and cupped down against the mandrel, meeting the first long edge at a substantially non-overlapping interface. In some embodiment, a thin-walled (about 0.5 to about 2 mm thick), substantially rigid, substantially smooth-surfaced, partial-cylindrical "temporary holder" with a diameter substantially equal to that of the intended outside diameter of the tube to be made (e.g., 8 mm) and with a length longer than that of the solid support and holders is used to comb the second long edge forward toward the first holder and then cup this long edge against the mandrel.

In some embodiments, the temporary holder structure may be shaped differently than a circular cylinder, having, for example, a cross-section of a partial square, partial hexagon, or other open or closed geometric shape. Then, the second holder may be brought into position as described above. In some embodiments, the temporary holder may then be pulled longitudinally out from between the two holders, using the portion of the temporary holder extending beyond the support and holders as a grip, before the second holder is pressed as far laterally as possible against the solid support, thereby guiding the second long edge to meet the first long edge at a substantially non-overlapping interface.

Latches, clamps, and/or alignment pins 19 (not shown) affixed atop and on both ends of each of the two holders are then closed, tightening the two holders against one another. In some embodiments, the latches may be any latching/clamping mechanism that is functionally equivalent to that of a cam-action type clamp, examples of which include C-clamps, spring clamps, tape, etc. In other embodiments, alignment pins (not shown) may be inserted longitudinally from both sides of and into both the first and second holder, functioning to clamp the holders together while simultaneously maintaining their alignment.

Further, in some embodiments, a linear array comprising a single or plurality of barbed felting needles 20 is advanced into the beveled lead-in of the holder and partially into the single, substantially rectangular slot, such that the needle tips do not yet contact the long edge of the first strip. In one embodiment, the non-barbed shafts of each of the felting needles are fixed into the array such that they directly abut one another, providing a tip-to-tip distance of approximately 1 mm. In this and related embodiments, the number of felting needles comprising the array will range from 1 to 250, depending on the length of tube to be made. In another embodiment, the felting needles may alternate between standard (forward) felting needles and inverted (reverse) felting needles. In a preferred embodiment, the array comprises a linear arrangement of 30 standard (forward) 42 gauge, chrome-plated triangular blade felting needles (e.g., from Groz Beckert). In such preferred embodiments, the tip-to-tip distance between needles is 4 mm. The needle array is designed such that the needles are capable of being held rigidly in place in their associated holes by clamping the needle array against a backstop, applying pressure against the L-shaped cranks on the ends of the needle shafts. Further, in this embodiment, the L-shaped cranks of each needle are fixed in the same orientation relative to the needle array, thereby ensuring that the three barbed faces of each of the triangular-bladed needles are oriented substantially identically. In this embodiment, the needle array is advanced electromechanically into the beveled lead-in using a computer-controlled linear actuator (e.g., Digit actuator, Ultra Motion, Cutchogue, N.Y.; Si2035 stepper motor controller, Applied Motion Products, Watsonville, Calif.). In other embodiments the needle array may be advanced manually, for example, by de-energizing the stepper motor of the linear actuator and turning the manual adjustment knob on the rear of the stepper motor.

In a next step of the method according to some embodiments, the needle array 20 may be programmed to advance repeatedly in and out of the single, rectangular slot, moving longitudinally along the length of the holder and strip with the completion of each in-and-out motion perpendicular to the strip. With each motion, the needles traverse and penetrate perpendicularly through both the first and second long edges of the strip, approaching and penetrating substantially tangent to the center of the strip's thickness 21 (i.e., tangent to a circle of 7 mm diameter, in the case of a tube intended to be 6 mm inside diameter and 8 mm outside diameter). In a preferred embodiment, the barbed portion of the needles penetrate approximately 1 cm across the nascent seam-line with each passage. Also in a preferred embodiment, the needle array moves approximately 1.33 mm longitudinally along the length of the strip following each in-and-out motion perpendicular to the strip, and needles penetrate back into the same hole locations an average of 6 times (for example). In other embodiments, the needles may penetrate back into the same hole locations different numbers of times, ranging from about 1 to about 20.

Figure 3:
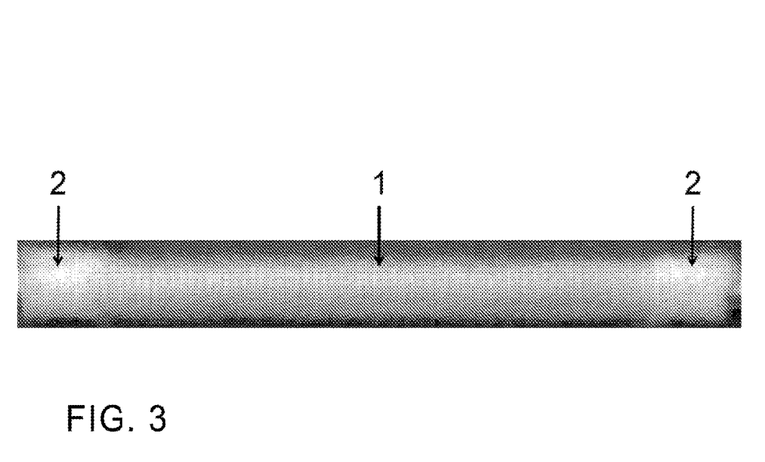
FIG. 3 shows an embodiment of a tubular structure made by processes and apparatuses disclosed herein comprising (1) nonwoven PGA and (2) nonwoven PET cuffs on both ends of the tubular structure.

In an exemplary embodiment, the needle array 20 is retracted to its initial position, the latches, clamps and/or alignment pins are opened, and the holders are removed, allowing for the tubular material (22 in FIGS. 2A and 2B, FIG. 3) to be removed from the device. In some embodiments, the tubular material formed as described above may be repositioned into the hemi-cylindrical groove 12, enclosed within the holder 14 and second holder 18, and subjected to additional needling (i.e., additional needle penetrations). Moreover, in some embodiments, the tubular material formed during the first needling may be rotated about one of more of its axes prior to or following repositioning into the hemi-cylindrical groove 12. The additional needling can be performed utilizing any combination of the same or a different number of needles, the same or different gauges or shapes of needles, the same or different numbers of needle penetrations, and/or the same or different needling patterns. As indicated above, in some embodiments the tube is comprised of two or more fibrous parts (e.g., 1 and 2 in FIG. 3).

The above-described embodiments can be implemented in any of numerous ways. For example, embodiments of designing and making the scaffolding structures disclosed herein may be implemented using hardware, software or a combination thereof. When implemented in software, the software code can be executed on any suitable processor or collection of processors, whether provided in a single computer or distributed among multiple computers.

Further, it will be appreciated that a computer may be embodied in any of a number of forms, such as a rack-mounted computer, a desktop computer, a laptop computer, or a tablet computer (i.e., processor). Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing, making and operating the coupling structures (and diffractive optical elements disclosed above)) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of this disclosure. The computer readable medium or media can be transportable, such that the program or programs stored thereon can be loaded onto one or more different computers or other processors to implement various aspects of the present disclosure.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods according to some embodiments of the disclosure and need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety.

Although a few variations have been described in detail above, other modifications are possible. For example, any logic flows depicted in the accompanying figures and/or described herein do not require the particular order shown, or sequential order, to achieve desirable results. Other implementations may be within the scope of at least some of the following exemplary claims.

As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to binding event determinative systems, devices and methods. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system for forming tubular scaffolds for tissue engineering, comprising:
   a mandrel with an outer circumference configured to receive a strip of scaffolding material wound there around;
   at least one first structure configured with at least one first recess configured to receive at least a first portion of the circumference of the mandrel with the wound scaffolding material;
   at least one second structure configured with at least one second recess configured to receive at least a second portion of the circumference of the mandrel with the wound scaffolding material;
   at least one channel provided along a length of the second structure and arranged between the internal surface of the second recess and an external surface of the second structure,
   wherein
   the at least one first structure and the at least one second structure are configured for mated arrangement such that upon mating the circumference of the mandrel having the strip of scaffolding material wound there around is substantially encompassed by the first and second recesses,
   the strip of scaffolding material wound around the circumference of the mandrel such that a first lengthwise edge of the strip is aligned immediately adjacent to a second lengthwise edge of the strip to form a tubular structure,
   the two adjacently positioned lengthwise edges forming a lengthwise boundary, the lengthwise boundary being arranged adjacent the channel;
   and
   at least one needle arranged adjacent the channel and configured for insertion through the channel to tangentially puncture the tubular structure proximate to and along the lengthwise boundary from at least one side of the lengthwise boundary such that a portion of one or more fibers from the strip near at least one of the lengthwise edges traverses the lengthwise boundary and intertwines with one or more fibers from the strip near the other lengthwise edge thereby forming a seam.

2. The system of claim 1, further comprising:
   an electromechanical linear actuator configured to at least one of:
   insert and retract the at least one needle through the channel repeatedly; and move the at least one needle longitudinally along the channel.

3. The system of claim 2, wherein the electromechanical linear actuator is further configured to position the at least one needle at a determined distance from the tubular structure prior to tangentially puncturing the tubular structure.

4. The system of claim 1, wherein the at least one needle comprises a plurality of needles.

5. The system of claim 4, wherein:
   the plurality of needles comprises needles with barbed triangular blades arranged in a linear array; and
   a face of each of the barbed triangular blades of the plurality of needles are oriented substantially identically.

6. The system of claim 1, further comprising:
a quarter-cylindrical third structure with a diameter corresponding to an outer diameter of the mandrel with the strip of scaffolding material wound thereon, the third structure configured to comb over one of the first lengthwise edge of the strip and the second lengthwise edge of the strip so as to align the first lengthwise edge of the strip and the second lengthwise edge of the strip immediately adjacent to each other to form the tubular structure.

7. The system of claim 4, wherein the plurality of needles are arranged in a predetermined pattern.

8. The system of claim 1, wherein the at least one needle is configured for advancing and retracting a plurality of times.

9. The system of claim 1, further comprising means configured for repetitive advancement and retraction of at least the tip of the at least one or more needles.

* * * * *